United States Patent [19]

Bell et al.

[11] 4,000,165

[45] Dec. 28, 1976

[54] 2,5-DI-LOWER-ALKYL-3,4-DI-(2-HYDROXY-2-PROPYL)FURAN COMPOUNDS

[75] Inventors: Malcolm R. Bell; Rudolf Oesterlin, both of East Greenbush, N.Y.

[73] Assignee: Sterling Drug Inc., New York, N.Y.

[22] Filed: Sept. 18, 1975

[21] Appl. No.: 614,478

[52] U.S. Cl. .............................. 260/347.8; 424/285
[51] Int. Cl.$^2$ ...................................... C07D 307/42
[58] Field of Search ................................ 260/347.8
[56] References Cited
FOREIGN PATENTS OR APPLICATIONS 812,999   9/1974   Belgium

OTHER PUBLICATIONS

Bradley et al., Chem. Abstracts vol. 50, 12946–12948 (12948b is pertinent) (1956).

*Primary Examiner*—Natalie Trousof
*Assistant Examiner*—Bernard Dentz
*Attorney, Agent, or Firm*—William G. Webb; B. Woodrow Wyatt

[57] ABSTRACT

2,5-Di-lower-alkyl-3,4-disubstituted-furans have antisecretory activity.

2 Claims, No Drawings

2,5-DI-LOWER-ALKYL-3,4-DI-(2-HYDROXY-2-PROPYL)FURAN COMPOUNDS

BACKGROUND OF THE INVENTION a. Field of the Invention

This invention relates to 2,5-di-lower-alkyl-3,4-disubstituted-furans.

b. Description of the Prior Art

The species, 2,5-dimethyl-3,4-diacetylfuran and 2,5-dimethyl-3,4-di-(2-hydroxy-2-propyl)furan, are disclosed in Belgian Patent No. 812,999, granted Sept. 30, 1974. Novitskii et al., Zh. Obshch. Khim. 34 (8), 2568 (1964) disclose 2,5-dimethyl-3,4-bis-hydroxymethylfuran.

SUMMARY OF THE INVENTION

This invention relates, in one composition of matter aspect, to 2,5-di-lower-alkyl-3,4-di-(2-hydroxy-2-propyl)furans having useful anti-secretory activity.

In a second composition of matter aspect, the invention relates to 2,5-di-lower-alkyl-3,4-diacetylfurans useful as intermediates for the preparation of the corresponding di-(2-hydroxy-2-propyl)furans.

DETAILED DESCRIPTION INCLUSIVE OF THE PREFERRED EMBODIMENTS

More specifically, the invention relates to 2,5-di-lower-alkyl-3,4-di-(2-hydroxy-2-propyl)furans having useful anti-secretory activity and having the formula:

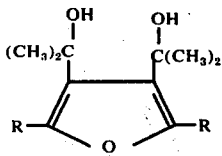

I where R represents lower-alkyl.

Also contemplated by the invention are 2,5-di-lower-alkyl-3,4-diacetylfurans useful as intermediates for the preparation of the compounds of formula I above and having the formula:

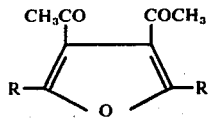

II where R has the meaning given above.

As used herein, the term lower-alkyl means saturated, monovalent, aliphatic radicals, including straight or branched-chain radicals, of from 1 to 4 carbon atoms as illustrated by methyl, ethyl, propyl, isopropyl, butyl, iso-butyl, t-butyl and the like.

The compounds of formulas I and II are prepared by cyclization under acidic conditions of a 1,2-di-RCO-1,2-diacetylethane of formula III and reaction of the resulting 2,5-di-R-3,4-diacetylfuran of formula II with a methyl magnesium halide.

The method is illustrated by the following reaction sequence:

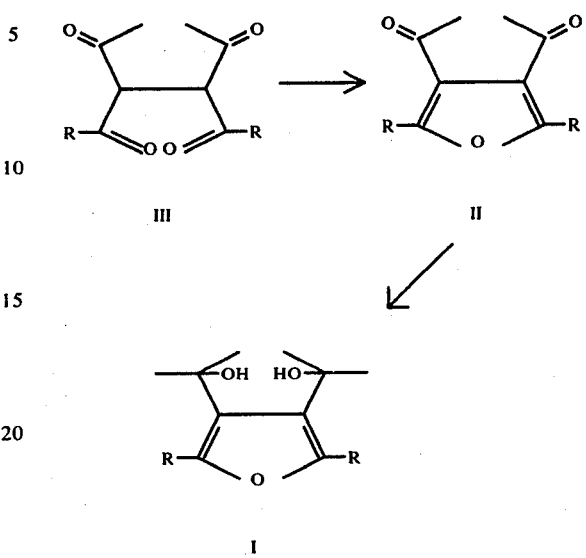

where R has the meanings given above.

Cyclization of the 1,2-di-RCO-1,2-diacetylethanes of formula III to the 2,5-di-R-3,4-diacetylfurans of formula II is carried out by treating a solution of the former with concentrated mineral acid at ambient temperature and isolation of the product from the reaction mixture.

Conversion of the 2,5-di-R-3,4-diacetylfurans of formula II to the 2,5-di-R-3,4-di-(2-hydroxy-2-propyl)furans of formula I is carried out by reaction of the former with two molar equivalents of a methyl magnesium halide in an inert organic solvent, for example diethyl ether, tetrahydrofuran, dioxane or dibutyl ether. The reaction is preferably carried out at a temperature in the range from 0° C. to around 50° C.

In a standard biological test procedure, described generally by Shay et al., Gastroenterology 5, 43 (1945) and 26, 906 (1954), the compounds of formula I have been found to possess anti-secretory activity and are thus useful as anti-secretory agents. Anti-secretory activity was determined in male albino Wistar rats weighing approximately 180 g. using the test procedure described as follows: the rats were divided into medicated groups of at least five rats each and control groups of 10 rats. The rats were medicated orally once daily for 2 days prior to stomach ligation and once again immediately following ligation. All drugs were administered as the free base, and control rats received only the vehicle of medication. The rats were housed individually in wire cages, food was withdrawn 48 hours prior to surgery, and water with withdrawn at the time of surgery. Laparotomy was performed under light ether anesthesia, the pyloric-duodenal junction was ligated, and the wound was closed with metal clips and sprayed with a protective surgical dressing. Five hours following surgery, the rats were sacrificed, the stomach was removed, and the gastric juice collected. The gastric fluid, was centrifuged, and total volume, color, and volume of solids were recorded. The pH of the gastric fluid was then determined on a Beckman pH meter, and the pH compared with a control.

The compounds of formula I were thus found to inhibit secretion of gastric fluids when administered orally at a dose of around 100 mg./kg. The compounds are preferably administered orally, and the amount of a particular compound to be administered, either alone or as the essential active ingredient in a formulation, will range from about 10 to about 200 mg./kg.

The actual determination of the numerical biological data definitive for a particular compound of formula I is readily determined by standard test procedures by technicians versed in pharmacological test procedures without the need for any extensive experimentation.

The compounds of formula I can be prepared for use by incorporation in unit dosage form as tablets or capsules for oral administration either alone or in combination with suitable adjuvants such as calcium carbonate, starch, lactose, sodium bicarbonate, sodium lauryl sulfate, sugar, dextrose, mannitol, cellulose, gum acacia, and the like. Alternatively, they can be formulated for oral administration in aqueous alcohol, glycol, or oil solutions or oil-water emulsions in the same manner as conventional medicinal substances are prepared. They can also be formulated for oral use with foodstuffs or admixed with foodstuffs for veterinary use.

The molecular structures of the compounds of the invention were assigned on the basis of study of their infrared, ultraviolet, and NMR spectra, and confirmed by the correspondence between calculated and found values for elementary analyses for the elements.

In the following examples illustrating the invention, all melting points are uncorrected.

EXAMPLE

To a slurry of 84.5 g. (2.0 moles) of a 57% mineral oil dispersion of sodium hydride in 1500 ml. of diethyl ether was added a solution of 200 ml. (2.0 moles) of 2,4-pentanedione in 200 ml. of diethyl ether over a period of two and one half hours. The mixture was stirred an additional thirty minutes, and then treated dropwise with a solution of 254 g. (1.0 mole) of iodine in about 2 liters of diethyl ether over a period of 6 hours. The mixture was allowed to stand overnight, and the solid which separated was then collected, washed once with diethyl ether, once with water, and dried to give 114.1 g. of 1,1,2,2-tetraacetylethane, m.p. 186°–206° C.

A mixture of 1.0 g. of 1,1,2,2-tetraacetylethane in 10 ml. of concentrated hydrochloric acid was stirred at room temperature for about 1 hour until a clear solution was obtained. The mixture was then poured onto ice and extracted with diethyl ether. The extracts were dried over sodium sulfate, taken to dryness, and the residue recrystallized from hexane to give 2,5-dimethyl-3,4-diacetylfuran, m.p. 75°–77° C.

A solution of 5.4 g. (0.03 mole) of 2,5-dimethyl-3,4-diacetylfuran in about 40 ml. of tetrahydrofuran was added dropwise to a stirred solution of 0.15 mole of methyl magnesium bromide in 50 ml. of ether. The mixture was warmed for about a half hour, then treated with 100 ml. of water, 50 ml. of 10% hydrochloric acid, and 100 ml. of ether. The mixture was extracted with ether, and the combined ether extracts were washed with water, dried over sodium sulfate and evaporated to dryness to give material which was recrystallized from benzene/pentane to give 6.1 g. of 2,5-dimethyl-3,4-di-(2-hydroxy-2-propyl)furan, m.p. 156°–158° C. as large cubic crystals. This material is polymorphic and can be obtained as needles from benzene/pentane (m.p. 136°–138° C.) or as a fine powder from pentane (m.p. 145°–149° C.).

In the above-described anti-secretory activity test, 2,5-dimethyl-3,4-di-(2-hydroxy-2-propyl)furan, on oral administration in rats, produced an increase in pH to 2.9 from 1.0 in control.

We claim:
1. A compound having the formula:

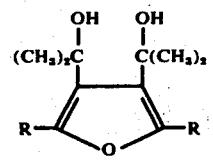

where R represents lower-alkyl.

2. 2,5-Dimethyl-3,4-di-(2-hydroxy-2-propyl)furan according to claim 1.

* * * * *

UNITED STATES PATENT AND TRADEMARK OFFICE
CERTIFICATE OF CORRECTION

PATENT NO. : 4,000,165
DATED : December 28, 1976
INVENTOR(S) : Malcolm R. Bell and Rudolf Oesterlin It is certified that error appears in the above—identified patent and that said Letters Patent are hereby corrected as shown below:

Column 2, line 57, "with withdrawn" should read --was withdrawn--.

Signed and Sealed this

Twenty-seventh Day of April 1982

[SEAL]

Attest:

GERALD J. MOSSINGHOFF

Attesting Officer

Commissioner of Patents and Trademarks